(12) United States Patent
Green et al.

(10) Patent No.: US 9,101,464 B2
(45) Date of Patent: Aug. 11, 2015

(54) ARTIFICIAL EYES AND MANUFACTURE THEREOF

(75) Inventors: Lewis Green, Sheffield (GB); Thomas George Fripp, Sheffield (GB); Lesley Elizabeth Gill, Manchester (GB)

(73) Assignee: The Manchester Metropolitan University, Manchester (GB)

(*) Notice: Subject to any disclaimer, the term of this patent is extended or adjusted under 35 U.S.C. 154(b) by 0 days.

(21) Appl. No.: 13/978,390

(22) PCT Filed: Jan. 5, 2012

(86) PCT No.: PCT/GB2012/050010
§ 371 (c)(1),
(2), (4) Date: Aug. 13, 2013

(87) PCT Pub. No.: WO2012/093257
PCT Pub. Date: Jul. 12, 2012

(65) Prior Publication Data
US 2013/0317609 A1 Nov. 28, 2013

(30) Foreign Application Priority Data
Jan. 5, 2011 (GB) .................................. 1100081.7

(51) Int. Cl.
*A61F 2/16* (2006.01)
*B05D 3/06* (2006.01)
*A61F 2/14* (2006.01)
*B29C 67/00* (2006.01)

(52) U.S. Cl.
CPC ............. *A61F 2/141* (2013.01); *B29C 67/0081* (2013.01)

(58) Field of Classification Search
CPC ...................... A61F 2/141; B29C 67/0081
USPC ..................... 427/2.24; 264/1.7; 623/6.64
See application file for complete search history.

(56) References Cited

U.S. PATENT DOCUMENTS

| 2,497,873 | A | | 2/1950 | Erpf |
| 5,733,333 | A | | 3/1998 | Sankey |
| 6,139,577 | A | | 10/2000 | Schleipman et al. |
| 6,143,026 | A | * | 11/2000 | Meakem ................. 128/898 |
| 2003/0017311 | A1 | * | 1/2003 | Garitano ................. 428/195 |
| 2005/0275137 | A1 | | 12/2005 | Stolpe et al. |
| 2006/0173541 | A1 | * | 8/2006 | Friel ...................... 623/6.64 |
| 2008/0046078 | A1 | * | 2/2008 | Singer .................... 623/6.64 |
| 2009/0186554 | A1 | | 7/2009 | Alfaro |

FOREIGN PATENT DOCUMENTS

| EP | 1264679 A2 | 12/2002 |
| GB | 2487055 A | 7/2012 |

(Continued)

OTHER PUBLICATIONS

EP Search Report dated Sep. 28, 2011 for corresponding EP application GB1100081.7.
EP Search Report reported Nov. 1, 2012 (searched Oct. 31, 2012) for related EP Application GB1211903.8.
Amended EP Search Report reported Dec. 12, 2012 (searched Oct. 31, 2012) for related EP Application GB1211903.8.

(Continued)

*Primary Examiner* — Cachet Sellman
(74) *Attorney, Agent, or Firm* — Olive Law Group, PLLC

(57) ABSTRACT

A method of manufacturing an artificial eye for fitting as a whole or partial replacement of a patient's original eye is provided. The method includes providing a digitally acquired image of an iris and transferring the image to a substrate comprising at least the frontal region of an artificial eye.

13 Claims, 5 Drawing Sheets

(56) References Cited

FOREIGN PATENT DOCUMENTS

| WO | WO2008086033 A1 | 7/2008 |
| WO | WO2012061124 A1 | 5/2012 |

OTHER PUBLICATIONS

International Search Report and Written Opinion mailed May 25, 2012 for corresponding PCT application No. PCT/GB2012/050010.

\* cited by examiner

ARTIFICIAL EYES AND MANUFACTURE THEREOF

CROSS REFERENCE TO RELATED APPLICATION

This application is a 35 USC 371 application of International PCT Patent Application No. PCT/GB2012/050010 filed on Jan. 5, 2012, and further claims priority to GB 1100081.7 filed Jan. 5, 2011, the entire contents of both are hereby incorporated by reference herein.

BACKGROUND

The present invention relates to artificial eyes (ocular prostheses) and methods of manufacture thereof. More particularly, the present invention relates to rapid manufacturing techniques for artificial eyes and artificial eyes produced by such techniques.

Artificial eyes have been prepared for patients whose eye(s) have been damaged due to injury or disease for several centuries. However, the techniques used remain skilled and labour intensive. Commonly, the prosthesis is made from acrylic plastics such as polymethylmethacrylate (PMMA) and this is encapsulated. Prior to encapsulation, maxillofacial prosthetists and ocularists simulate the colour of the iris and sclera using individual hand-painting techniques with the patient present (or from an image of the patient's eye). A variety of artists media are used which are applied by pencils, crayons, cotton or a brush. This technique requires inherent artistic ability and is time consuming and expensive. The result is dependent upon operator ability and experience.

Various proposals have been made to decrease the cost of prosthesis manufacturing by utilising modern digital imaging and CADCAM techniques. For example US20060173541 (Friel) discloses the use of digital imaging of an iris in conjunction with use of techniques such as selective laser sintering, stereo lithography to manufacture a bespoke prosthesis. However, the approach disclosed is still relatively complex requiring a number of separate components to manufacture the finished artificial eye.

The present invention seeks to overcome or at least mitigate the problems of the prior art.

SUMMARY

A first aspect of the present invention provides a method of manufacturing an artificial eye for fitting as a whole or partial replacement of a patient's original eye, the method comprising the steps of:
  a) providing a digitally acquired image of an iris; and
  b) transferring the image to a substrate comprising at least the frontal region of an artificial eye.

Preferably there is a further step f) intermediate steps a) and b) of overlaying the image onto a 3D CAD model of an artificial eye.

In step b) the image is preferably transferred to the substrate as an inherent part of the forming of the substrate in the 3D printer. This has been found to be a particularly effective way of producing artificial eyes in a cost-effective manner. The colouration of the features of the eye (veins and/or iris) can advantageously be improved (be better defined) if the coloured features are configured to print to a predetermined depth below a surface layer of the substrate.

A second aspect of the present invention provides an artificial eye for fitting as a whole or partial replacement of a patient's original eye comprising a powder material bound together by a binder to form a shaped solid substrate, the binder being selectively coloured in at least in a region thereof to simulate at least an iris portion of an eye.

A third aspect of the present invention provides an artificial eye for fitting as a whole or partial replacement of a patient's original eye comprising a shaped substrate upon at least a region of which dye-sublimated ink is applied to simulate at least an iris of an eye.

The artificial eyes and the method of the present invention have been found to provide a relatively low cost and effective alternative to traditional manufacturing methods.

Preferred and/or optional features of the above three aspects of the present invention are disclosed in the dependent claims appended hereto.

Embodiments of the present invention will now be described in detail with reference to the accompanying drawings in which:

DETAILED DESCRIPTION

Figure 6:
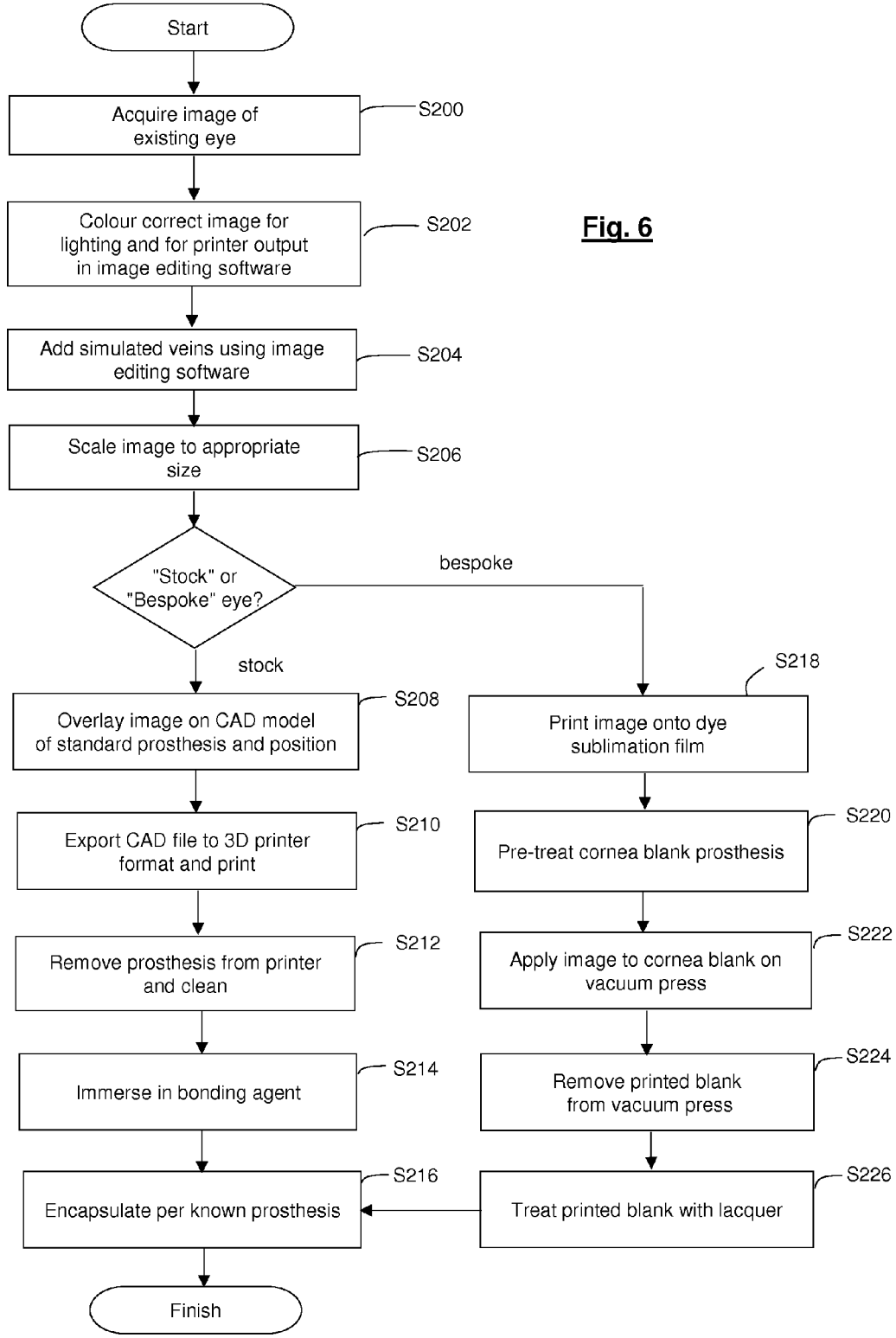
FIG. 6 is a flow chart illustrating a manufacturing method according to another embodiment of the present invention for manufacturing the prostheses of FIGS. 1, 2 and 3.

With reference to in particular FIG. 6, manufacturing methods according to two embodiments of the present invention are illustrated, in which certain steps are common, and other steps are not as described below.

The method of both embodiments of the present invention commences with the acquisition of an image of the visible portion of an existing eye at step S200. This image is preferably taken using a high quality digital camera such as a single lens reflex (SLR) camera. The image may be of a particular patient's eye before being replaced, may be of a patient's other eye that is not being replaced (if the eye to be replaced is injured to the extent that an image may not be acquired), or if the artificial eye is to be a "stock" eye it may simply be of any person's eye in order to be used with a collection that is representative of a number of different general eye colours and sizes for subsequent "off the shelf" use.

Figure 4:
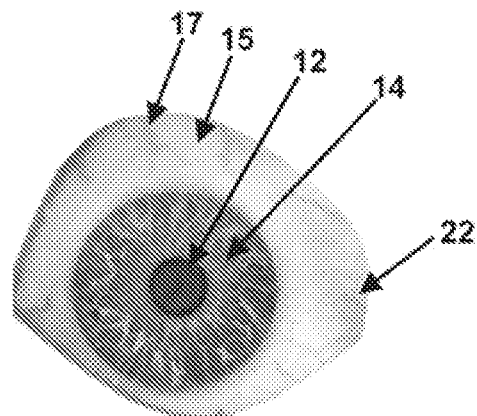
FIG. 4 is a captured digital image of an eye.

With reference to FIG. 4 the image 22 that is acquired is incomplete since only a portion of the eye in situ can be made visible at any time. The image 22 comprises a pupil 12, iris 14, and sclera 15 having a particular pattern of veins 17 visible thereon. At step S202 the image is edited using suitable photo manipulation software such as Adobe Photoshop® At this stage, the iris 14 and pupil 12 are separated from the remainder of the image and the image is colour corrected to remove a colour cast that may be present due to the lighting conditions under which the photograph is acquired. In addition, the image 22 is adjusted to account for the particular colour profile of the printer upon which the image will be output. In particular, the image is typically acquired and stored as an RGB image whereas the printer prints using a CYMK colour palette and appropriate corrections should be made.

Figure 5:
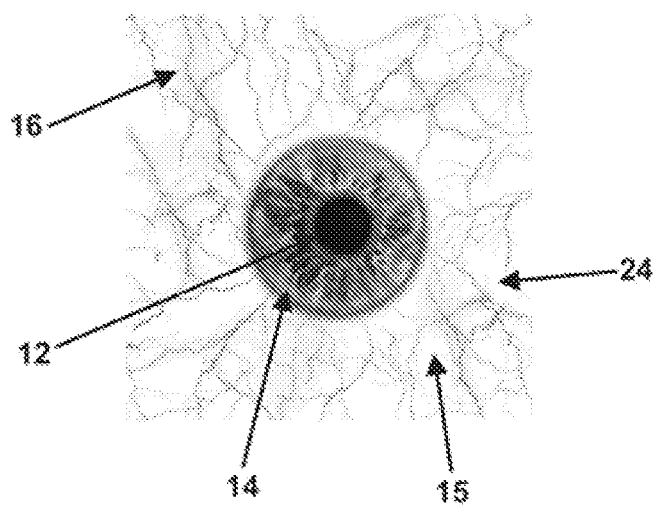
FIG. 5 is a digital image that has been manipulated and is ready for subsequent use.

At step S204 simulated veins 16 are applied to the image and the image canvas is extended to a sufficient area for subsequent coverage of an artificial eye blank to provide a manipulated image 24 as illustrated in FIG. 5. In particular, a suitable Photoshop brush may be used to apply the simulated veins. In a variant of the process the veins 17 from the acquired image may be retained, and simulated veins 16 may be matched thereto for the remainder of the canvas.

At step S206 the manipulated image 24 is scaled to an appropriate size. In selecting the size, it is preferable that consideration is made for the apparent enlargement of the features of the eye that will occur as a result of optical effects caused by the subsequent encapsulation process, as well as a general desire to have the iris 14 of the artificial eye appear slightly smaller than the iris of the patient's "real" eye since this tends to draw attention away from the artificial eye and it is therefore less noticeable.

Figure 1:
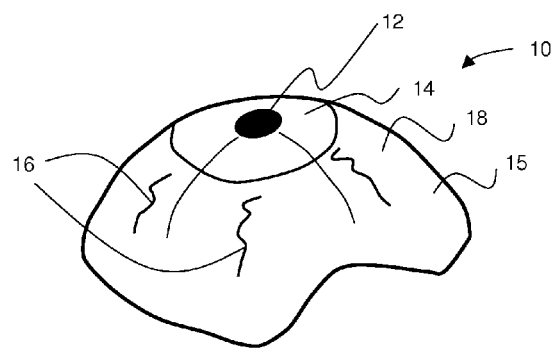
FIG. 1 is a perspective view of a domed artificial eye (ocular prosthesis) according to a first embodiment of the present invention.
Figure 2:
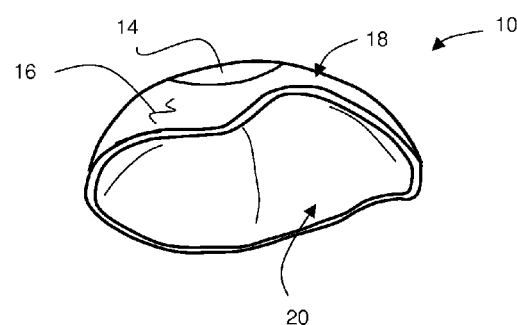
FIG. 2 is a perspective view of the artificial eye of FIG. 1 from a different angle.

At this point, the process diverges dependent upon the type of artificial eye that is required. Considering the first or "stock" process:

This process is primarily to be used for the production of stock or "off the shelf" eyes that may be produced in a range of standard sizes and colours, and which may be used as a temporary artificial eye, or a lower cost permanent eye, e.g. to be used in developing countries. In addition to the entirely off the shelf approach, a standard sized and shaped prosthesis may be used in conjunction with an image which has been matched to a particular patient by the acquisition process set out above. A finished stock eye according to this embodiment is shown in FIGS. 1 and 2 and is generally indicated by the numeral 10. The eye 10 is generally in the shape of a hollow dome, having an outer convex surface 18 and an inner concave surface 20.

Eyes 10 of this type may be used in conjunction with a so-called "orbital implant". These are a substantially hemispherical replacements for an eye that has been removed that are manufactured from a natural porous material such as coral, or an equivalent artificial material, which subsequently becomes ingrown with the blood vessels and the tissue of the patient and is therefore integrated into the body. An artificial eye 10 of the type shown in FIGS. 1 and 2 can then be secured as the visible "cover" over this orbital implant and mounted thereto by use of a suitable small peg that locates within the orbital implant.

Further manufacture of this form of artificial eye 10 is as follows:

At step S208 the scaled image produced at S206 is overlaid on a CAD model of the required prosthesis and is positioned at an appropriate location with pupil 12 at the frontal portion of the model. In a preferred embodiment the image is also overlain on a reverse (concave) face of the model in register the same image on the convex face.

In a preferred embodiment, Magics rapid prototyping software, produced by Materialise of Leuven, Belgium is used for this stage of the process with the CAD model being in STL format. In one variant, the scaling of the image 24 is undertaken at this stage in Magics, rather than or in addition to the scaling that is undertaken at step S206 in Photoshop. A close-up image of the patient's real eye may be used at this stage to ensure that a size and position good match is achieved for the artificial eye. The Magics software may then export the finished model in a suitable CAD file format for manufacturing on a 3D printer.

At step S210 in a preferred embodiment of the present invention, a Z Corporation Spectrum model 510 3D printer is used and Magics exports the CAD file in the proprietary ZPR or ZCP format that is suitable for use with this type of printer.

Z Corporation produces a range of 3D printers that also includes models 450 and 650, which function using a proprietary process that builds up a 3D product in layers from powder material, and are also suitable for use in the method of the present invention. The printer has four print heads that "print" a binder material into powder selectively in conjunction with coloured inks (one head for each colour) to produce coloured 3 dimensional objects, in a manner akin to a standard inkjet printer. The printers have a resolution upwards of 300×300 dpi in the X and Y direction and a layer thickness of as little as 0.01 mm (Z direction). The way in which the colour is mixed in with the binder means that the colour penetrates a distance into the eye itself and is an intrinsic part of the finished eye, rather than a layer on the surface.

In this embodiment, a silica powder having the designation ZB150 and a binder having the designation ZB60 are used. Both are supplied by Z Corporation. This powder is bleached to produce objects that are by default white or substantially so. The artificial eyes are preferably printed using this printer with the outermost (anterior) portion of the eye 10 when fitted uppermost on the print bed since this produces a strong finished eye. As the print bed is substantially larger than a single artificial eye, multiple eyes can be manufactured simultaneously in an X and Y direction, and may also be stacked on top of each other in the Z direction.

In a preferred embodiment, as a result of superimposing the image 24 onto both the convex and concave faces of the CAD model the image is printed on both faces 18 and 20 of the finished 3D article, and in view of the degree of translucency of the material at this thickness, the resultant artificial eye appears to have a more vivid, realistic, colouring.

Once the printing process is complete, at step S212 the artificial eyes 10 are removed from the bed of powder and are cleaned using a stiff brush or by sand blasting and are then air brushed with compressed air to remove any remaining dust and particles.

At step S214 the artificial eye 10 is then immersed in a low viscosity bonding agent that is substantially colourless, for example cyanoacrylate, in this embodiment Procure PC08 produced by Cyanotech of Dudley, UK. This product has the advantage of being an approved substance for use in the manufacturing of medical devices.

Once removed from the bonding agent and when curing is complete, at step S216 the artificial eye 10 may then be encapsulated in an acrylic material using a suitable known technique of the type that has been employed for prior art PMMA artificial eyes, before being fitted to a patient.

In the second embodiment, the manufacturing steps after S206 differ and are as follows:

At step S218 the scaled and colour corrected image is printed onto a transfer material, which in this embodiment is dye sublimation film using dye sublimation ink in an inkjet printer. A preferred ink is Artrainium ink supplied by Sawgrass of Sheffield, UK in CYMK and light cyan light magenta colours.

Figure 3:
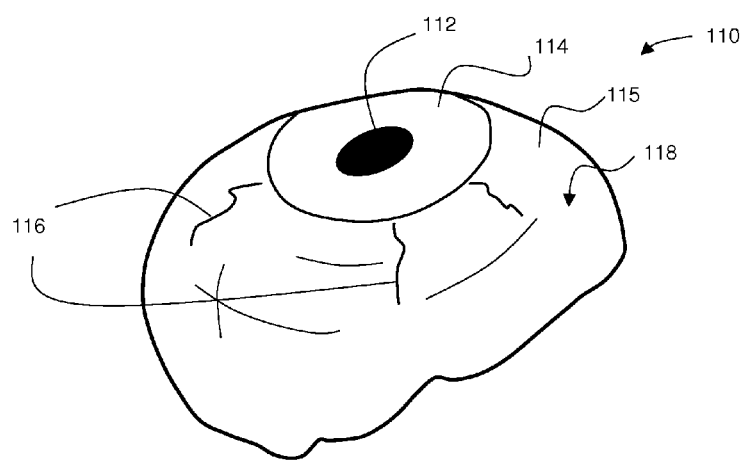
FIG. 3 is a perspective view of an artificial eye according to a second embodiment of the present invention.

In this embodiment a cornea blank has the general solid domed shape of the finished artificial eye 110 shown in FIG. 3, but no colouring, is manufactured from PMMA using a known process. The blank of this embodiment is termed "bespoke" because the rear (anterior) thereof is shaped in accordance with a cast that has been taken of a particular patient's eye socket, again using a known process, and thus is specifically intended for use with that patient.

The cornea blank is then pre-coated with an adhesion promoter such as Digicoat as supplied by Octi-tech Limited of Sheffield, UK, which is then wiped off and followed by application of a sublimation coat that may also be supplied by Octi-tech Limited in the Digicoat range. This process occurs at step S220.

At step S222 the pre-treated cornea blank is then loaded at a predetermined location into a vacuum press for the dye sublimation ink to be transferred onto the blank. A suitable vacuum press for this to be achieved is a Pictaflex PF480/6 model as supplied by I-Sub of Kettering, UK. This press has a sufficiently large bed that an array of blank prostheses may be arranged at suitable locations that correspond to printed images on the sublimation film, and the transfer may then simultaneously have images transferred to them. In a preferred embodiment, a supporting grid (e.g. of sheet metal with an array of apertures provided therein) is preferably placed around the individual images to prevent the sublimation film from sagging during the image application process set out below.

In the vacuum press machine, the chamber is heated, the bed supporting the blank prosthesis is raised and a vacuum is generated in order to suck the sublimation film onto the blank. The heat causes the sublimation ink to be transferred from the film onto the prosthesis in an appropriate location. After an appropriate dwell time, the vacuum is removed and the film and blank separated and the press is allowed to cool.

Table 1 below sets out examples of various heat and dwell time parameters that have been used. Example 5 has been found to provide the best results.

TABLE 1

|  | Standard Setting | Ex. 1 | Ex. 2 | Ex. 3 | Ex. 4 | Ex. 5 | Ex. 6 |
|---|---|---|---|---|---|---|---|
| Pre-heat temp (° C.) | 120 | no pre-heat | no pre-heat | no pre-heat | no pre-heat | no pre-heat | no pre-heat |
| Pre-heat time (sec) | 20 | 0c | 0 | 0 | 0 | 0 | 0 |
| Fill temp (° C.) | 135 | 135 | 135 | 145 | 135 | 135 | 135 |
| Vacuum time (sec) | 8 | 8 | 8 | 12 | 12 | 12 | 12 |
| Air temp (° C.) | 190 | 190 | 200 | 220 | 180 | 190 | 200 |
| Transfer temp* (° C.) | 170 | 180 | 190 | 200 | 160 | 175 | 185 |
| Print time (sec) | 150 | 160 | 170 | 180 | 160 | 120 | 120 |
| Release time (sec) | 15 | 15 | 15 | 20 | 15 | 5 | 5 |
| Cooling time (sec) | 15 | 15 | 30 | 35 | 30 | 30 | 30 |
| Unload (sec) | 60 | 60 | 60 | 60 | 35 | 35 | 35 |

*Transfer temp = ideal temperature to transfer the image from film to eye

The blank is then removed from the vacuum press at step S224 and a clear lacquer is then applied to the image that has been transferred so to minimise the bleeding of colours at step S226, to produce the artificial eye 110 illustrated in FIG. 3 A currently preferred lacquer is "Very high temperature lacquer" supplied by Hycote of Oldham, UK.

Like features of this eye 110 are designated by like numerals compared to FIGS. 1 and 2, but with the addition of the prefix "1".

At step S216, the printed blank is then encapsulated at step S216 in the same known manner as with the method of the first embodiment, ready for the artificial eye to be fitted to a patient.

FIGS. 7 to 10 illustrate an artificial eye and manufacturing process according to a third embodiment of the present invention, in which like parts are labelled by like numerals with the addition of the suffix '.

The eye 10' and process of the third embodiment is a variation of that of the first embodiment, so only differences from the first embodiment are discussed in detail.

Figure 7:
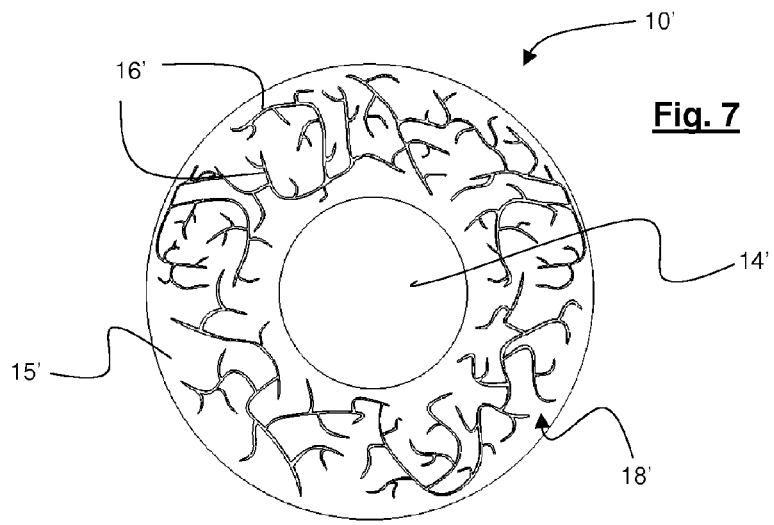
FIG. 7 is a plan view of a partially formed domed artificial eye (ocular prosthesis) according to a third embodiment of the present invention.
Figure 8:
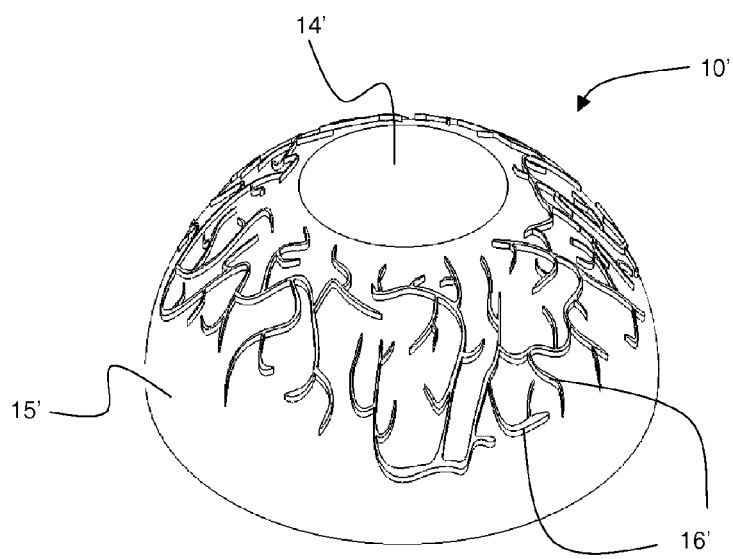
FIG. 8 is a perspective view of the partially formed domed artificial eye of FIG. 7.

Referring to FIGS. 7 and 8 an alternative way of building up the colouration of veins 16' is shown. In this embodiment, instead of printing the vein colour on the surface layer of powder, a predetermined depth of material (e.g. 0.2-1 mm) is coloured below the surface parallel to the posterior-anterior axis, as the eye is built up. This has been found to improve the colour and clarity of the veins. A similar approach (not shown) is also used to improve iris colouration. It will be appreciated that although the veins are illustrated standing proud of the sclera 15' to explain this approach, in reality, both would be built up together at the same level.

Figure 9:
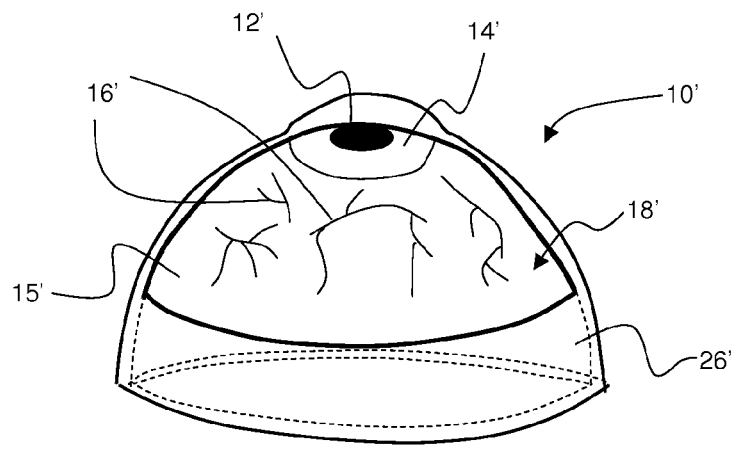
FIG. 9 is a perspective view of domed artificial eye according of FIG. 7 at a later stage of manufacture.

It will also be noted in FIGS. 7 and 8 that the 3D printed portion of the eye 10' has a regular domed shaped that is a full or part hemisphere. Forming a part hemisphere enables a transparent "skirt" portion 26' of poly methyl methacrylate (PMMA) encapsulation material to be formed as part of the encapsulation process as shown in FIG. 9.

Figure 10:
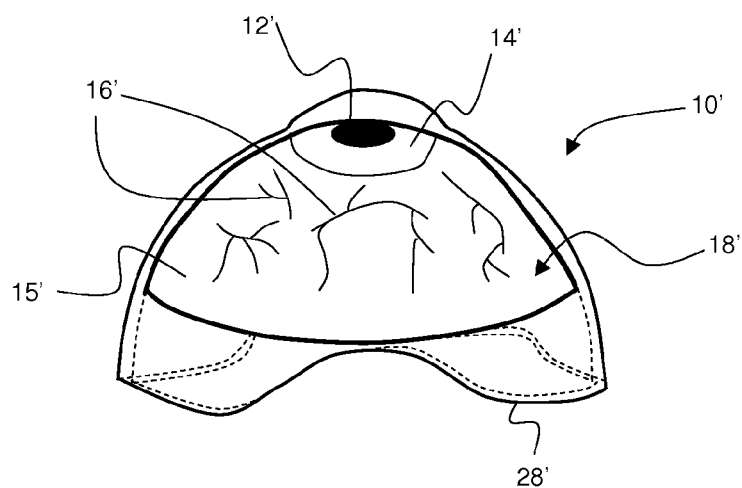
FIG. 10 is a perspective view of domed artificial eye according of FIG. 7 at a still later stage of manufacture.

This approach is advantageous in certain instances as it then allows the perimeter free edge 28' of the skirt 26' to be removed (e.g by milling or grinding) to customise the eye 10' to a particular patient after encapsulation has been completed, as illustrated in FIG. 10.

It will be appreciated that numerous changes may be made within the scope of the present invention. For example certain steps of the processes may be altered in their order; various steps may be taken at different times and in different locations. Other suitable 3D printers, dye sublimation materials, and vacuum presses, and image manipulation techniques and software may be used. The blanks/substrate used need not have a wholly domed shape. For example, the iris region may be substantially flat, and the finished domed shape built up from the encapsulation material.

It will be appreciated that terms such as front and rear, upper and lower are used for ease of explanation, and should not be regarded as limiting.

It will further be appreciated that the methods of both embodiments of the present invention result in a cost effective way in which artificial eyes may be produced at significantly less cost than prior art techniques, which means that higher quality artificial eyes may be supplied in developing countries where previously the cost would be prohibitive. The resultant artificial eyes have been found to be of at least similar or of higher quality than those produced by prior art methods

The invention claimed is:
1. A method of manufacturing an artificial eye for fitting as a whole or partial replacement of a patient's original eye, the method comprising the steps of:

a) providing a digitally acquired image of an iris; and
b) transferring the image to a substrate comprising at least the frontal region of an artificial eye,
wherein in step b) the image is transferred to a substrate by a 3D printer.

2. A method according to claim 1 wherein the frontal region is non-planar.

3. A method according to claim 2, wherein the frontal region is dome shaped.

4. A method according to claim 1 further comprising a step c) intermediate steps a) and b) wherein the image of the iris is colour corrected.

5. A method according to claim 1, further comprising a step d) intermediate steps a) and b) of artificially adding lines representative of veins to a sclera portion of the image.

6. A method according to claim 1 further comprising a step e) intermediate steps a) and b) of scaling the image to an appropriate size.

7. A method according to claim 6 wherein in step e) the image is scaled to account for the optical effects of a subsequent encapsulation process.

8. A method according to claim 6 wherein in step e) the image is scaled to ultimately appear smaller than an iris of a patient's other original eye.

9. A method according to claim 1, comprising a further step f) intermediate steps a) and b) of overlaying the image onto a 3D CAD model of an artificial eye.

10. A method according to claim 9 wherein in step f) the image is overlaid on an inner and outer face of the 3D CAD model.

11. A method according to claim 1 wherein in step b0 the image is transferred to the substrate as an inherent part of forming of the substrate using the 3D printer.

12. A method according to claim 11 wherein at least part of a coloured portion of the image is configured to print to a predetermined depth below a surface layer of the substrate as the eye is built up.

13. A method according to claim 11 wherein the 3D printer utilises powder and a binder material built up layer on layer to form the substrate, wherein the powder is a silica powder, and further wherein the powder is a substantially white powder.

\* \* \* \* \*